United States Patent [19]

Bigg

[11] 4,282,225

[45] Aug. 4, 1981

[54] THIAZOLE DERIVATIVES USEFUL IN THERAPY AS ANTI-DEPRESSANT AGENTS

[75] Inventor: Dennis C. H. Bigg, Jouy en Josas, France

[73] Assignee: Synthelabo, Paris, France

[21] Appl. No.: 117,990

[22] Filed: Feb. 4, 1980

[30] Foreign Application Priority Data

Feb. 12, 1979 [FR] France .................. 79 03431

[51] Int. Cl.³ .................. C07D 277/60; C07D 239/00; C07D 277/00; A61K 31/425; A61K 31/505
[52] U.S. Cl. ..................................... 424/251; 548/154; 548/155; 424/270; 544/278
[58] Field of Search ................ 548/155, 154; 424/270, 424/251; 544/278

[56] References Cited

U.S. PATENT DOCUMENTS

| | | | |
|---|---|---|---|
| 2,853,872 | 12/1974 | Wei et al. ............................. | 548/154 |
| 3,671,533 | 6/1972 | Houlihan et al. .................... | 548/154 |
| 4,059,588 | 11/1977 | Baklien et al. ...................... | 548/155 |

*Primary Examiner*—Nicholas S. Rizzo
*Attorney, Agent, or Firm*—Wegner & Bretschneider

[57] ABSTRACT

Thiazole derivatives of general formula (I)

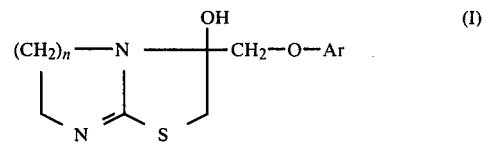

in which n is 1 or 2 and Ar represents a phenyl radical unsubstituted or substituted by one or more substituents selected from halogen atoms, the radical $CF_3$, the phenyl radical straight or branched chain alkyl radicals having 1 to 4 carbon atoms, and cycloalkyl radicals having 3 to 6 carbon atoms, and their pharmaceutically acceptable acid addition salts are useful in therapy as anti-depressive agents. They are prepared by reacting the thiazole

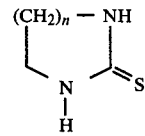

with a ketone $X-CH_2-CO-CH_2O-Ar$ (III) (X is a leaving group, such as halogen).

6 Claims, No Drawings

THIAZOLE DERIVATIVES USEFUL IN THERAPY AS ANTI-DEPRESSANT AGENTS

The present invention relates to thiazole derivatives, useful in therapy.

The thiazole derivatives of this invention are compounds of general formula (I)

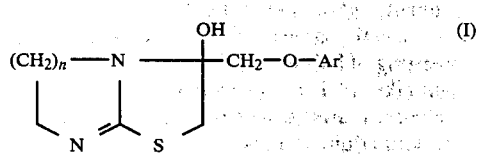

in which n is 1 or 2 and Ar represents a phenyl radical unsubstituted or substituted by one or more substituents selected from halogen atoms, the $CF_3$ radical, the phenyl radical, straight or branched chain alkyl radicals having 1 to 4 carbon atoms, and cycloalkyl radicals having 3 to 6 carbon atoms, and their pharmaceutically acceptable acid salts.

The thiazole derivatives defined above have an asymmetric carbon atom. Their optically active isomers and racemates are included in the above definition.

The preferred thiazole derivatives are those in which Ar is a phenyl radical unsubstituted or substituted by 1, 2 or 3 substituents selected from halogen atoms, preferably bromine, chlorine and fluorine atoms, methyl, isopropyl, cyclohexyl, phenyl and $CF_3$ radicals.

The invention provides a process for preparation of the thiazole derivatives which comprises reacting a thiourea of formula (II)

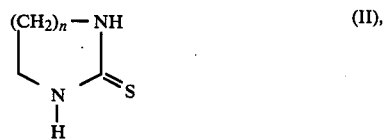

n being as defined above
with a ketone of formula (III)

$$X-CH_2-CO-CH_2O-Ar \quad (III),$$

Ar being as defined above,
in which X is a halogen atom, preferably chlorine or bromine, or any other leaving group. This reaction is advantageously carried out in solution in an inert solvent, e.g. in acetone, and at ambient temperature.

The ketones of formula (III) can be prepared by known methods described e.g. in Organic Syntheses Coll. vol. 3 p. 119, in Swiss Pat. Nos. 235,943 and 235,944 and in French Pat. No. 6691 M. The ketones (III) can be used as obtained, without purification, for the preparation of the thiazole derivatives. The thiazole derivatives will normally be obtained in the form of a salt with an acid of formula HX, especially wherein X is a halogen atom. The preferred salts are thus hydrochlorides. The salt can be converted to the free base in a manner known per se.

The following Examples illustrate the invention. Analyses and IR and NMR spectra confirm the structure of the compounds obtained.

EXAMPLE 1

3-hydroxy-3-[(2-methylphenoxy)methyl]-2,3,5,6-tetrahydroimidazo [2,1-b]thiazole hydrochloride. (n=1, Ar=2—$CH_3$—$C_6H_4$).

6.5 g. (0.0636 mole) of N,N'-ethylenethiourea in 800 cm.$^3$ of acetone and 79.4 g of (2-methylphenoxy)methyl chloromethyl ketone in 100 cm.$^3$ of acetone were introduced into a 1 liter Erlenmeyer flask. The reaction mixture is agitated at ambient temperature for 20 hours. The creamy solid obtained is filtered and washed with acetone and then with diethyl ether. The solid is recrystallised in a 2:1 mixture of n-propanol and acetone, m.p 157°–158° C.

EXAMPLE 2

3-hydroxy-3-[(2,4-dichlorophenoxy)methyl]-6,7 (5H)-dihydrothiazolo[3,2-a]pyrimidine hydrochloride. (n=2,Ar=2,4—$Cl_2$—$C_6H_3$)

5.8 g. mole (0.05 mole) of 3,4,5,6-tetrahydropyrimidinethiol in 1200 cm.$^3$ of acetone and 44 g. (0.173 mole) of (2,4-dichlorophenoxy)methyl chloromethyl ketone in 80 cm.$^3$ of acetone are introduced into a 2 liter Erlenmeyer flask. The reaction mixture is agitated at ambient temperature for 4 hours and then left to stand for 48 hours. A beige clear solid is recovered, which is recrystallised from acetone to yield a white solid, m.p. 183° C.

In the following Table thiazole derivatives prepared by way of example are shown. They were prepared as salts with 1 mole HCl, but can of course readily be converted to the corresponding free base, and thence to any other desired acid addition salt. These free bases and all pharmaceutically acid addition salts thereof are therefore specific preferred triazole derivatives. In the Table "$C_6H_5$" represents a phenyl radical and "$C_6H_4$", "$C_6H_3$" and "$C_6H_2$" residues of phenyl radicals bearing 1, 2 and 3 substituents, respectively.

TABLE

| Compound | n | Ar | m.p. of hydrochloride salt, °C. |
|---|---|---|---|
| 1 | 1 | $C_6H_5$ | 127–8 |
| 2 | 1 | 4-Cl—$C_6H_4$ | 143.5–144.5 |
| 3 (Example 1) | 1 | 2-$CH_3$—$C_6H_4$ | 157–8 |
| 4 | 1 | 3-$CF_3$—$C_6H_4$ | 146–7 |
| 5 | 1 | 3,4-$Cl_2$—$C_6H_3$ | 153–4 |
| 6 | 1 | 2,6-$(CH_3)_2$—$C_6H_3$ | 190–1 |
| 7 | 1 | 4-$C_6H_5$—$C_6H_4$ | 194–5 |
| 8 | 1 | 3-F—$C_6H_4$ | 144–5 |
| 9 | 1 | 4-Br—$C_6H_4$ | 156–7 |
| 10 | 1 | 3-Cl—$C_6H_4$ | 154–155 |
| 11 | 1 | 2-isopropyl-$C_6H_4$ | 134–135.5 |
| 12 | 1 | 2,6-$Cl_2$—$C_6H_3$ | 163* |
| 13 | 1 | 2-cyclohexyl-$C_6H_4$ | 185* |
| 14 | 1 | 2-$C_6H_5$—$C_6H_4$ | 169–170 |
| 15 | 1 | 2,5-$Cl_2$—$C_6H_3$ | 150* |
| 16 | 1 | 2,4,5-$Cl_3$—$C_6H_2$ | 165* |
| 17 | 1 | 2-Cl—$C_6H_4$ | 147–148 |
| 18 | 1 | 2-Br—$C_6H_4$ | 148–149 |
| 19 | 1 | 2,4-$Cl_2$—$C_6H_3$ | 155* |
| 20 (Example 2) | 2 | 2,4-$Cl_2$—$C_6H_3$ | 183* |
| 21 | 2 | 4-$C_6H_5$—$C_6H_4$ | 193–5 |
| 22 | 2 | 4-Br—$C_6H_4$ | 192–4 |
| 23 | 2 | 2-$C_6H_5$—$C_6H_4$ | 188–190 |

*Melting point determined by differential thermal analysis. The other melting points were determined by the Tottoli method.

The thiazole derivatives have been tested pharmacologically and shown to have anti-depressive activity.

Their toxicity has been determined in the mouse intraperitoneally. The $LD_{50}$ ranges from 100 to more than 1000 mg/kg. The antidepressive activity has been determined by the test of activity against reserpine-induced ptosis (Gouret, C. et al., J. Pharmacol. (Paris) 8, 333–350 (1977). Mice (males, CD1 Charles River Strain, France, weighing 18 to 22 g.) received simultaneously a dose of the thiazole derivative or of solvent as control, intraperitoneally, and 4 mg./kg. of reserpine subcutaneously. 60 minutes thereafter the degree of palpebral ptosis was assessed by a rating scale of 0 to 4 for each mouse. For each dose the mean rating and the percentage difference from the control sample were calculated. For each thiazole derivative the $AD_{50}$ (dose which reduces by 50% the mean rating for ptosis from the control sample) was determined graphically. The $AD_{50}$ varies from 3 to 10 mg./kg. for intraperitoneal administration. The results of the tests show that the thiazole derivatives are useful antidepressant agents, i.e. for the treatment of depression.

The triazole derivatives can be formulated in any appropriate way for administration, e.g. orally, parenterally or rectally in the form of tablets, dragees, gel capsules, or drinkable or sterile injectable solutions. They will frequently be formulated as pharmaceutical compositions comprising the thiazole derivative in association with a pharmaceutical excipient (which term includes an inert diluent or carrier).

The daily dosage of thiazole derivative can be from 5 to 200 mg.

I claim:

1. Thiazole derivatives, in the form of racemates or optically active isomers, of the formula

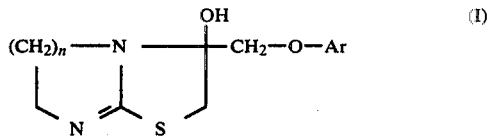

in which n is 1 or 2 and Ar represents phenyl which is unsubstituted or substituted by one or more substituents which are the same or different, selected from the group consisting of halogen, $CF_3$, phenyl, straight or branched chain alkyl of 1 to 4 carbon atoms, and cyclohexyl of 3 to 6 carbon atoms, and their pharmaceutically acceptable acid addition salts.

2. Derivatives according to claim 1 in which Ar is a phenyl radical unsubstituted or substituted by from 1 to 3 substituents selected from halogen atoms and methyl, isopropyl, cyclohexyl and phenyl radicals.

3. As derivatives according to claim 1, 3-hydroxy-3-[(2-methylphenoxy)methyl]-2,3,5,6-tetrahydroimidazo[2,1-b]thiazole and its pharmaceutically acceptable acid addition salts.

4. A derivative according to claim 3 in the form of a hydrochloride salt.

5. A anti-depressant pharmaceutical composition comprising a thiazole derivative as claimed in claim 1 in association with a pharmaceutically acceptable excipient.

6. A method of treating a patient for depression which comprises administering to the patient a therapeutically effective dose of a thiazole derivative as claimed in claim 1.

* * * * *